United States Patent [19]

Hopper

[11] 3,997,605
[45] Dec. 14, 1976

[54] PREPARATION OF FORMAMIDE COMPOUNDS

[75] Inventor: Roger J. Hopper, Akron, Ohio

[73] Assignee: The Goodyear Tire & Rubber Company, Akron, Ohio

[22] Filed: May 19, 1975

[21] Appl. No.: 578,460

[52] U.S. Cl. .................................................. 260/561 S
[51] Int. Cl.² ............. C07C 103/02; C07C 103/30
[58] Field of Search ................................ 260/561 S

[56] References Cited

UNITED STATES PATENTS

| | | | |
|---|---|---|---|
| 3,674,856 | 7/1972 | Chang et al. .................. | 260/561 S |
| 3,699,122 | 10/1972 | Kohn .............................. | 260/561 S |
| 3,699,163 | 10/1972 | Kohn .............................. | 260/553 A |
| 3,705,135 | 12/1972 | Wolfinger ....................... | 260/561 S |
| 3,780,001 | 12/1973 | Son ................................. | 260/79.5 A |

*Primary Examiner*—C. Davis
*Attorney, Agent, or Firm*—F. W. Brunner; J. A. Rozmajzl

[57] ABSTRACT

N-cyclohexyl-formamide is reacted with sulfur monochloride in the presence of an organic hydrogen chloride acceptor to form N,N'-di(cyclohexyl)-N,N'-dithiobis(formamide), which can then be reacted with sulfuryl chloride or chlorine to form N-chlorothio-N-cyclohexyl-formamide which can then be reacted with an olefin to form a retarder having the following structural formula.

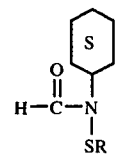

9 Claims, No Drawings

PREPARATION OF FORMAMIDE COMPOUNDS

This invention relates to the preparation of N,N'-di(-cyclohexyl)-N,N'-dithiobis(formamide); N-chlorothio-N-cyclohexyl-formamide and N-(2-chlorocyclohexyl-thio)-N-cyclohexyl-formamide.

Those skilled in the art are continually searching for new retarders which can be used as scorch inhibitors in the sulfur vulcanization of rubbers.

It is an object of this invention to provide a novel retarder. It is also an object to provide intermediate compounds which can be used in the preparation of the retarder. In addition, it is an object of this invention to provide processes for preparing the retarder and the intermediates.

The objects of the present invention are accomplished by reacting N-cyclohexyl-formamide with sulfur monochloride in the presence of an organic hydrogen chloride acceptor to form N,N'-di(cyclohexyl)-N,N'-dithiobis(formamide), which can then be reacted with sulfuryl chloride or chlorine to form N-chlorothio-N-cyclohexyl-formamide which can then be reacted with an olefin having the structure

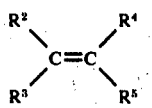

to form a retarder having the following structural formula

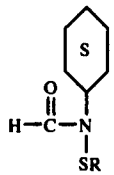

wherein R is selected from the group consisting of

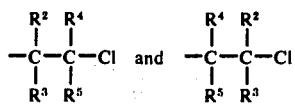

wherein $R^2$, $R^3$, $R^4$ and $R^5$ are selected from the group consisting of hydrogen and alkyl radicals having from 1 to 10 carbon atoms and $R^2$ and $R^4$ can be taken together to represent $-(CH_2)_{n'}-$ where $n'$ is 3 to 6.

The retarders are illustrated by compounds where R is 2-chloroethyl, 2-chloro-1-propyl, 1-chloro-2-propyl, 2-chloro-1-butyl, 1-chloro-2-butyl, 2-chlorocyclohexyl or 2-chloro-1-decyl. Preferred are compounds where R is 2-chloroethyl, 2-chloro-1-propyl, 2-chloro-1-butyl or 2-chlorocyclohexyl.

All of the chloroalkylated compounds are retarders, i.e., they can be used to inhibit prevulcanization (scorch) in diene polymers compounded with sulfur.

Preferred olefins are ethylene and terminal olefins, i.e., where $R^2$, $R^3$, and $R^4$ are hydrogen. Preferred as terminal olefins are propylene, butene-1, pentene-1, hexene-1, and octene-1.

None of the reactions described herein are limited by temperature considerations other than the normal ones, i.e., decomposition temperatures of reactants and reaction products should obviously be avoided, and naturally, as reaction temperatures decrease, the rate of reaction will decrease as well.

All of the reactions involve the use of an inert organic solvent which is preferably a somewhat polar solvent such as benzene, chlorobenzene, a chlorinated hydrocarbon, e.g., dichloromethane or chloroform.

The function of the organic acid acceptor in the condensation reaction is to form a neutral salt with acidic hydrogen chloride.

The organic hydrogen chloride acceptors include tertiary amines of the formula

wherein $R^1$ and $R^2$ are alkyl radicals having from 1 to 6 carbon atoms and $R^3$ is selected from the group consisting of phenyl, benzyl and alkyl radicals having 1 to 6 carbon atoms. The organic hydrogen chloride acceptors also include pyridine or an alkyl substituted pyridines wherein the alkyl group is either methyl or ethyl, for example, collidine. Such compounds react with hydrogen chloride to form salts of the types

and

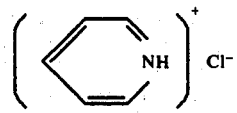

The use of organic hydrogen chloride acceptors is a common practice and well known to those skilled in the art.

To prepare the dithiobis(formamide) derivative one mole of sulfur monochloride is added to a stirred solution of 2 to 2.5 moles of N-cyclohexyl-formamide and 2 to 3 moles of the organic hydrogen chloride acceptor in an inert solvent. The rate of addition and external cooling are adjusted to keep the exothermic reaction within the desired temperature range (−10° C. to +50° C., preferably 0° to 25° C). During the reaction, a precipitate of the amine hydrochloride salt is formed. This precipitate is removed by filtration at the end of the reaction and the filtrate washed first with dilute hydrochloric acid, then with water until the washings are neutral. The organic layer is preferably dried over a suitable drying agent (e.g., sodium or magnesium sulfate), and the solvent removed under vacuum. The residue, a yellow to orange oil is mixed with petroleum ether to precipitate the dithiobis(formamide) derivative as a white solid.

To prepare N-chlorothio-N-cyclohexyl(formamide), the dithiobis formamide is chlorinated with an equivalent amount of chlorine or sulfuryl chloride in an inert solvent (preferably a chlorinated hydrocarbon such as tetrachloroethylene, dichloromethane, or chloroform). Although an excess amount of the chloro compound can be used, it is preferred that an equivalent amount be charged since an excess amount can result in undesirable side reactions. The reaction is carried out at −10° C. to +60° C., preferably at 20° C. to 40° C. With sulfuryl chloride as the chlorinating agent, the reaction may be considered complete when sulfur dioxide evolution ceases. The N-chlorothio-N-cyclohexylformamide is not usually isolated from the reaction solution. The solution may be conveniently assayed by standard iodometric procedures, or by proton magnetic resonance spectroscopy.

The addition of N-chlorothio-N-cyclohexyl formamide to olefins is carried out at −30° C. to +100° C., preferably at 0° to 35° C. and most conveniently at room temperature. With low boiling olefins it is often preferable to carry out the reaction under pressure (<1000 psi) above the boiling point of the olefin. The reaction may be carried out in an inert solvent or with excess olefin as the solvent. The reaction occurs more readily in polar solvents such as dichloromethane or chloroform. The molar ratio of N-chlorothio-N-cyclohexyl formamide to olefin may be from .01 to 1, preferably from 0.8 to 1. Since no by-products are formed, the reaction product is isolated by simply removing the solvent or solvents.

EXAMPLE 1

To prepare N,N'-di-(cyclohexyl)-N,N'-dithiobis (formamide), 33.5 grams of sulfur monochloride was added over 15 minutes to a stirred solution of 63.6 grams of N-cyclohexyl formamide and 39.6 grams of pyridine in 400 milliliters of benzene at 15° C. The mixture was then stirred for 2½ hours at 15° C. to 20° C., filtered, and the filtrate washed with 300 milliliter portions of water, dilute HCl, then twice more with water. After drying over sodium sulfate and filtering, the solvent was removed under vacuum leaving a semisolid residue. This was stirred with 60 milliliters of petroleum ether, filtered, and washed with 40 milliliters of petroleum ether. After drying, 23 grams of white solid, with a melting point of 125° C. to 127° C. was obtained. Analysis for C, H, N, and S were in agreement with the theoretical percentages.

EXAMPLE 2

To prepare N-chlorothio-N-cyclohexylformamide, 25.0 milliliters of a 0.855 molar solution of chlorine in CCl$_4$ was mixed with a solution of 6.77 grams of N,N'-dithiobis-(formamide) in 35 milliliters of dichloromethane. After stirring 45 minutes at room temperature in a closed flask, the solution stood overnight. Total volume of the solution was 65.0 milliliters. Evaporation of solvents, under vacuum, from 40.2 milliliters of the solution gave 4.98 grams (99%) of a yellow liquid.

EXAMPLE 3

To prepare N-(2-chlorocyclohexylthio)-N-cyclohexyl-formamide, the 4.98 grams of yellow liquid from Example 2 was mixed with 10 milliliters of cyclohexene and allowed to stand overnight at room temperature in a flask capped with a drying tube. Removal of excess cyclohexene at 50° C./water aspirator vacuum gave 7.00 grams (97.6%) of pale yellow viscous liquid. A portion of this was diluted with dichloromethane, passed through a bed of charcoal, and the dichloromethane removed. Elemental analysis for C, H, N, S, and Cl gave percentages in agreement with the theoretical amounts.

Attempts have been made to react N-methyl-formamide and N-tert.butyl-formamide with sulfur monochloride in the presence of an organic hydrogen chloride acceptor to form N,N'-di(methyl) — and N,N'-di(-tert.butyl)-N,N'-dithiobis(formamide) respectively. Although the N,N'-di(cyclohexyl)-N,N'-dithiobis(formamide) is easily separated from the reaction medium by crystallization, it has been impossible to separate the methyl or tert.butyl analogues, if indeed, they are formed at all, from their respective reaction media. Attempts to make and isolate products from formamide and N-ethylformamide were also unsuccessful.

The N-(2-chlorocyclohexylthio)-N-cyclohexylformamide product of Example 3 has been found to be effective as a retarder, that is, a scorch inhibitor in a natural rubber polymer containing a sulfur vulcanization system.

While certain representative embodiments and details have been shown for the purpose of illustrating the invention, it will be apparent to those skilled in this art that various changes and modifications may be made therein without departing from the spirit or scope of the invention.

I claim:

1. A process of preparing N,N'-di(cyclohexyl)-N,N'-dithiobis(formamide) comprising reacting N-cyclohexylformamide with sulfur monochloride in the presence of an organic hydrogen chloride acceptor.

2. A process of preparing N-chlorothio-N-cyclohexyl-formamide comprising reacting N,N'-di(cyclohexyl)-N,N'-dithiobis(formamide) with a chloro compound selected from the group consisting of sulfuryl chloride and chlorine.

3. A process of preparing a compound having the following structural formula

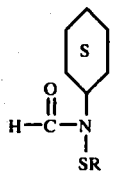

comprising reacting N-chlorothio-N-cyclohexyl-formamide with an olefin having the structure

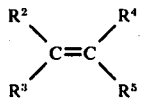

wherein R is selected from the group consisting of

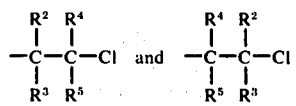

and wherein R$^2$, R$^3$, R$^4$ and R$^5$ are selected from the group consisting of hydrogen and alkyl radicals having from 1 to 10 carbon atoms and R$^2$ and R$^4$ can be taken together to represent —(CH$_2$)$_{n'}$ —, wherein $n'$ is 3 to 6.

4. A compound selected from the group consisting of N,N'-di(cyclohexyl)-N,N'-dithiobis(formamide); and compounds having the following structural formula

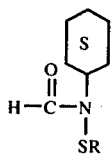

wherein R is selected from the group consisting of

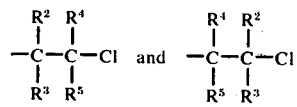

wherein $R^2$, $R^3$, $R^4$ and $R^5$ are selected from the group consisting of hydrogen and alkyl radicals having from 1 to 10 carbon atoms and $R^2$ and $R^4$ can be taken together to represent $—(CH_2)_{n'}—$ where $n'$ is 3 to 6.

5. The process of claim 1 wherein 2 to 2.5 moles of N-cyclohexyl formamide and 2 to 3 moles of organic hydrogen chloride acceptor are charged per mole of sulfur monochloride and wherein the reaction temperature is from $-10°$ C. to $+50°$ C.

6. The process of claim 2 wherein the reaction temperature is from $-10°$ C. to $+60°$ C.

7. The process according to claim 3 wherein the molar ratio of the formamide reactant to the olefin is from 0.01/1 to 1/1 and wherein the reaction temperature is from $-30°$ C. to $+100°$ C.

8. The process of claim 7 wherein the molar ratio is from 0.8/1 to 1/1.

9. A process of preparing N-chlorothio-N-cyclohexyl-formamide comprising reacting N-cyclohexylformamide with sulfur monochloride in the presence of an organic hydrogen chloride acceptor to form N,N'-di(cyclohexyl)-N,N'-dithiobis(formamide), and reacting the dithiobis product with a chloro compound selected from the group consisting of sulfuryl chloride and chlorine.

* * * * *